(12) United States Patent
Washburn et al.

(10) Patent No.: US 7,745,447 B2
(45) Date of Patent: Jun. 29, 2010

(54) SUBSTITUTED THIENO[3,2-D]PYRIMIDINES AS NON-BASIC MELANIN CONCENTRATING HORMONE RECEPTOR-1 ANTAGONISTS

(75) Inventors: William N. Washburn, Titusville, NJ (US); Saleem Ahmad, Wall, NJ (US); Khehyong Ngu, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 416 days.

(21) Appl. No.: 11/586,147

(22) Filed: Oct. 25, 2006

(65) Prior Publication Data

US 2007/0093508 A1 Apr. 26, 2007

Related U.S. Application Data

(60) Provisional application No. 60/730,453, filed on Oct. 26, 2005.

(51) Int. Cl.
 *C07D 495/04* (2006.01)
 *A61K 31/519* (2006.01)
 *A61P 25/22* (2006.01)
 *A61P 3/04* (2006.01)
 *A61P 3/10* (2006.01)

(52) U.S. Cl. .................... 514/260.1; 544/278
(58) Field of Classification Search ............... 544/278; 514/260.1
See application file for complete search history.

(56) References Cited

FOREIGN PATENT DOCUMENTS

| WO | WO 03/033476 | 4/2003 |
|---|---|---|
| WO | WO 2004/092181 | 10/2004 |
| WO | WO 2005/042541 | 5/2005 |
| WO | WO 2005/047293 | 5/2005 |
| WO | WO 2005/103039 | 11/2005 |

OTHER PUBLICATIONS

Vippagunta et. al. (Advanced Drug Delivery Systems, 2001, 48, 3-26).*
ScienceDirect- Bioroganic & Medicinal Chemsitry Letters, 2006, 16(19), p. 1.*
Borowsky, B. et al., "Antidepressant, anxiolytic and anorectic effects of a melanin-concentrating hormone-1 receptor antagonist", Nature Medicine, vol. 8, No. 8, pp. 825-830 (Aug. 2002).
Kowalski, T.J. et al., "Melanin-concentrating hormone-1 receptor antagonism decreases feeding by reducing meal size", European Journal of Pharmacology, vol. 497, pp. 41-47 (2004).
Kowalski, T.J. et al., "Therapeutic potential of melanin-concentrating hormone-1 receptor antagonists for the treatment of obesity", Expert Opin. Investig. Drugs, vol. 13, No. 9, pp. 1113-1122 (2004).
Takekawa, S. et al., "T-226296: a novel, orally active and selective melanin-concentrating hormone receptor antagonist", European Journal of Pharmacology, vol. 438, pp. 129-135 (2002).
Ulven, T. et al., "6-Acylamino-2-aminoquinolines as Potent Melanin-Concentrating Hormone 1 Receptor Antagonists. Identification, Structure-Activity Relationship, and Investigation of Binding Mode", J. Med. Chem., vol. 48, pp. 5684-5697 (2005).
Carpenter, A.J. et al., "Novel benzimidazole-based MCH R1 antagonists", Bioorganic & Medicinal Chemistry Letters 16, pp. 4994-5000 (2006).
Warshakoon N. C. et al., "Design and synthesis of substituted quinolines as novel and selective melanin concentrating hormone antagonists as anti-obesity agents", Bioorganic & Medicinal Chemistry Letters 16, pp. 5207-5211 (2006).

* cited by examiner

*Primary Examiner*—Susanna Moore
(74) *Attorney, Agent, or Firm*—Maureen S. Gibbons

(57) ABSTRACT

The present application provides compounds, including all stereoisomers, solvates, prodrugs and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I.

1 Claim, No Drawings

SUBSTITUTED THIENO[3,2-D]PYRIMIDINES AS NON-BASIC MELANIN CONCENTRATING HORMONE RECEPTOR-1 ANTAGONISTS

RELATED APPLICATION

This application claims priority benefit under Title 35 §119 (e) of U.S. Provisional Application No. 60/730,453, filed Oct. 26, 2005, the contents of which are herein incorporated by reference.

BACKGROUND

Several lines of pharmacological and genetic evidence support the role of Melanin Concentrating Hormone Receptor-1 (hereafter "MCHR1") as a modulator of food intake and body weight. Central administration of MCH increases food intake and body weight both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes.

Small molecule MCHR1 antagonists have been shown to cause weight loss in rodent weight and feeding models after both oral and intraperitoneal administration; Eur. J. Pharmacol., 438, 129-135, 2002, Nat. Med., 8, 825-830, 2002, Eur. J. Pharmacol., 497, 41-47, 2004.

Numerous non-peptide MCHR1 antagonists have been disclosed. The scope of the genus for each reflects a common perception regarding the criteria required for ligand recognition as MCHR1 agonists. A recent review of MCHR1 patent disclosures emphasized the commonality of these structures by the following description; "Ubiquitous throughout the MCH patent literature are molecules consisting of a central scaffold to which linkers to an aryl or heteroaryl group and a basic amino functionality are attached" (T. J. Kowalski and M. D. MacBriar, Expert Opin. Investig. Drugs 13, 1113-1122, 2004). Pharmacophore models of these geni consistently envision a presumed prerequisite electrostatic interaction between a basic amine center of the antagonist ligand and aspartic acid 123 of the receptor which presumably is envisaged to emulate the mandatory interaction between arginine 14 of MCH peptide agonists with aspartic acid 123 of the MCHR1 receptor. (T. Ulven, J. Med. Chem. 2005, 48, 5684-5697) However, incorporation of this basic amine in a MCHR1 antagonist increases substantially the probability of binding to off-target ion-channels and biogenic amine receptors.

Herein we describe a series of novel high affinity selective MCHR1 antagonists that were obtained by replacement of the basic amine moiety described in WO 03/033476 with non-basic polar functionalities. Moreover, this structural modification results in unexpected ablation of binding to other biogenic amine receptors as well as binding to the HERG receptor in the heart. The reduction/abolition of affinity for the HERG receptor is especially important since ligand occupancy is associated with initiation of fatal arrythmias.

DETAILED DESCRIPTION

The present application provides compounds, including all stereoisomers, solvates, prodrugs and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I.

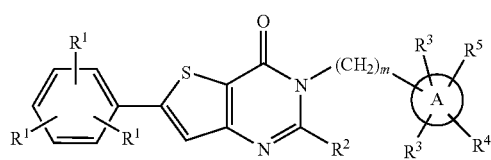

I wherein

A is selected from the group consisting of phenyl and heteroaryl;

$R^1$ is independently selected from the group consisting of hydrogen, halogen, lower alkyl, lower cycloalkyl, aryl, $CF_3$, CN, $NR^7R^7$, $OR^6$ and $SR^6$;

$R^2$ is selected from the group consisting of hydrogen and lower alkyl;

$R^3$ is independently selected from the group consisting of hydrogen or lower alkyl;

$R^4$ is selected from the group consisting of hydroxyl or $G-D^2-Z_n$, wherein $R^4$ and $R^5$ may be taken together to form a ring of 4 to 7 atoms;

$R^5$ is selected from the group consisting of hydrogen, hydroxyl, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ and $COR^6$;

m is an integer from 0 to 1;

n is an integer from 1 to 3;

G is selected from the group consisting of a direct bond, O, S and $CR^7R^7$;

$D^2$ is selected from the group consisting of a direct bond, lower alkyl, lower cycloalkyl and a 4 to 6-membered non-basic heterocycle;

when A is phenyl, Z is heteroaryl;

when A is heteroarvi, Z is selected from the group consisting of hydrogen, halogen, Hydroxyl, lower alkoxy, lower cycloalkyl, lower cycloalkoxy, $OCOR^6$, $OCONR^7R^7$, CN, $CONR^7R^7$, $OSO_2R^6$, $SR^6$, $SOR^6$, $SO_2R^6$, $NR^7COR^7$, $NR^7CONR^7R^7$, $NR^7CO_2R^7$, $COR_2R^7$, heterocycle, heteroaryl, $OPO(OR^6)_2$, $NR^7SO_2R^6$ and $COR^6$;

$R^6$ is independently selected from the group consisting of lower alkyl, lower cycloalkyl, heterocycle and heteroaryl; and $R^7$ is independently selected from the groun consisting of hydrogen, lower alkyl, lower cycloalkyl and heterocycle, wherein two $R^7$ and the atom to which they are attached may optionally form a ring of 4 to 7 atoms.

DEFINITIONS

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

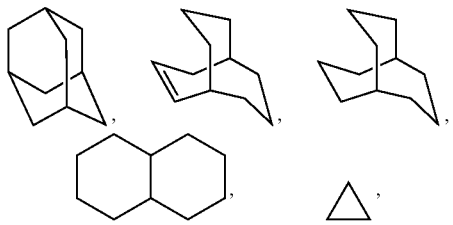

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

The term "heterocyclo", "heterocycle", "heterocyclyl" or "heterocyclic ring", as used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A.

R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein.

The term "alkanoyl" as used herein alone or as part of another group refers to alkyl linked to a carbonyl group.

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or "Aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

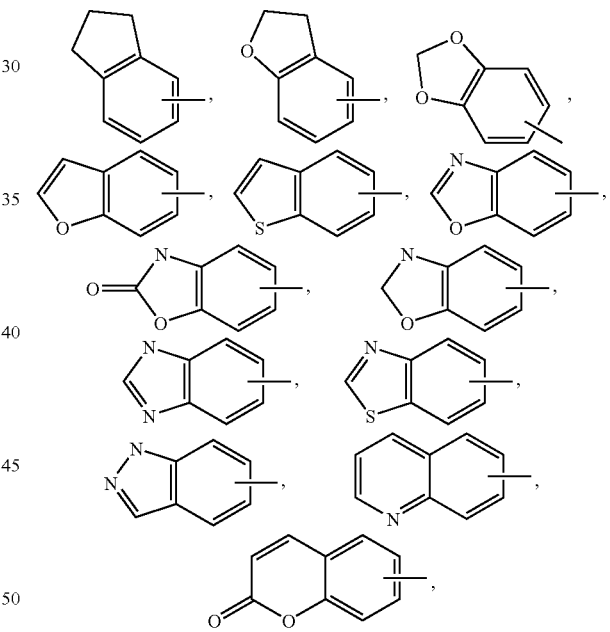

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature 1982-1995* 1996, Elsevier Science, Inc., Tarrytown, N.Y.; and references therein. Further, "heteroaryl", as defined herein, may optionally be substituted with one or more 5 substituents such as the substituents included above in the definition of "substituted alkyl" and "substituted aryl". Examples of heteroaryl groups include the following:

and the like.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalcyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The compounds of formula I of the application can be prepared as shown in the following reaction schemes and description thereof, as well as relevant published literature procedures that may be used by one skilled in the art. Exemplary reagents and procedures for these reactions appear hereinafter and in the working Examples.

ABBREVIATIONS

The following abbreviations are employed herein:
Ph=phenyl
Bn=benzyl
t-Bu=tertiary butyl
Me=methyl
Et=ethyl
TMS=trimethylsilyl
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3$N=triethylamine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point

Methods of Preparation

As summarized in Scheme 1, compounds of formula I may be prepared by either condensing compounds of formula 2 with compounds of formula 3 to generate the thiophenopyrimidone central bicyclic moiety in situ or via alkylation/arylation of compounds of formula 18 with alkylating agents of formula 19 or arylating agents such as borates of formula 24. Depending on the particular molecule of formula I being prepared, $R^4$ can either be fully completed or elaborated after assemblage of the core structure of formula I.

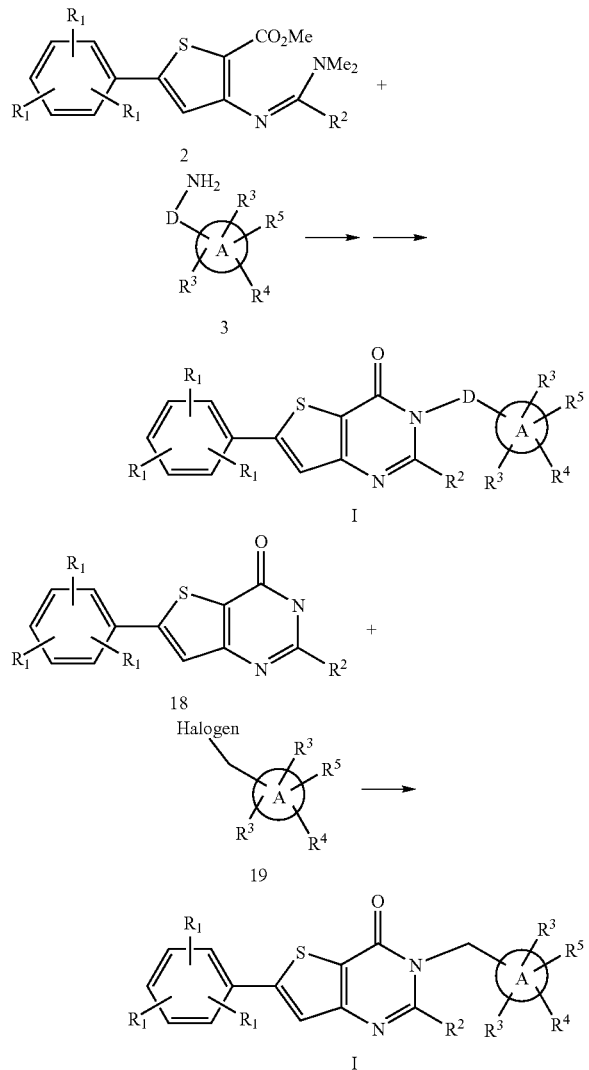

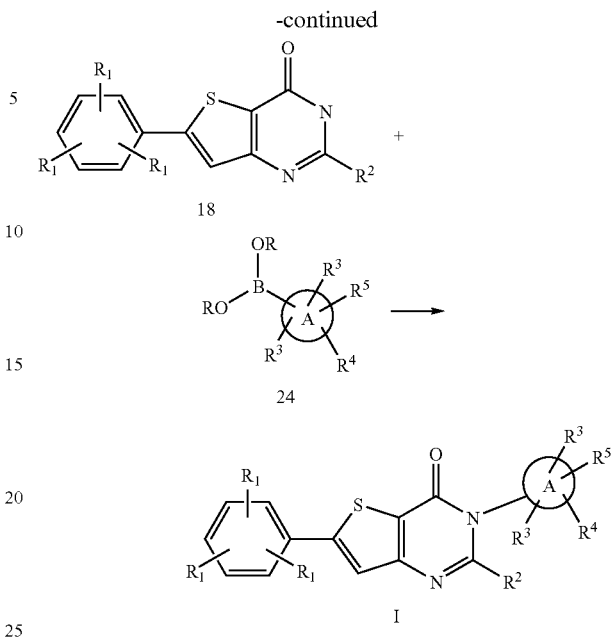

Specifically, compounds of formula I may be prepared by condensing compounds of formula 2 with compounds of formula 3 in a solvent such as hot EtOH (Scheme 2). Compounds of formula 2 can be prepared as described in WO2003/033476 by heating compounds of formula 4 with dimethylformamide dimethyl acetal. Preparation of compounds of formula 4 is described in WO 1998/49899. Amines of formula 3 for which D is a bond may be prepared by reduction of nitro aromatics of formula 5 either by catalytic hydrogenation using a catalyst such as Pd/C in a solvent such as EtOH or by reduction with $SnCl_2$ in a solvent such EtOAc. Compounds of formula 5 where G=O or S and D is a bond can be prepared by alkylation of the corresponding phenol or thiophenol of formula 6 with 20 an appropriate alkylating agent of formula 7 in the presence of a base such as $Cs_2CO_3$ or $K_2CO_3$ in a solvent such as DMF by employing procedures readily known to those skilled in the art. Alternatively compounds of formula 5 can be prepared by heating alkali metal salts of compounds of formula 6 with epoxides of formula 7a thermally or preferably by microwave in a solvent such as 15% $H_2O/MeCN$ containing $NaH_2PO_4$. Compounds of formula 5 can be also prepared by heating compounds of formula 8 with preformed sodium salts of compounds of formula 9 in a solvent such as DMF.

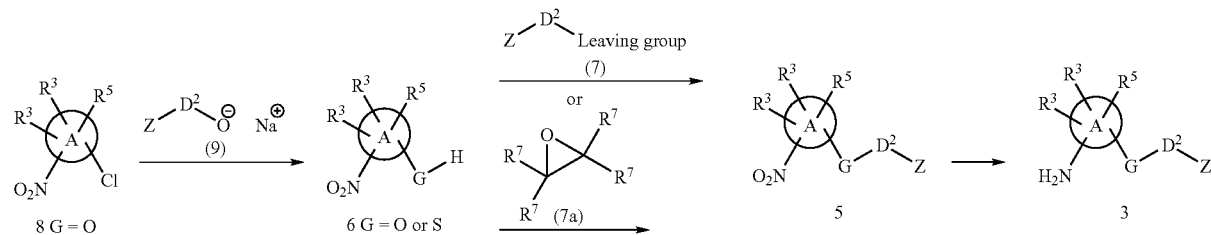

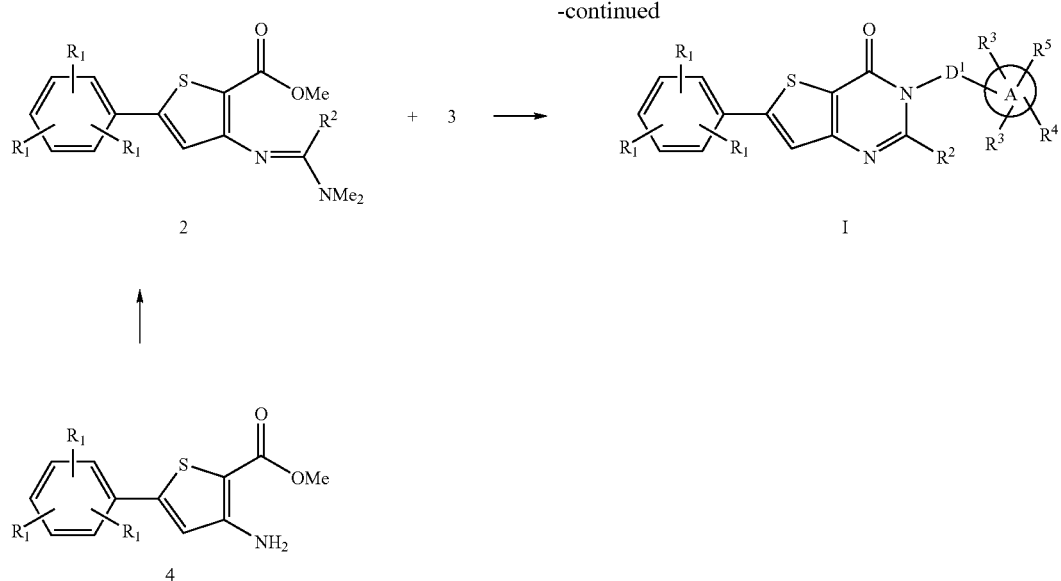

Compounds of formula I where G=alkylidine and D is a bond (Scheme 3) can be prepared by condensation of compounds of formula 2 with compounds of formula 3 which had been prepared as previously described by reduction of compounds of formula 5'. Compounds of formula 5' can be prepared by derivitization of amines of formula 9 or alcohols of formula 10 employing procedures readily known to those skilled in the art. Amines of formula 9 and alcohols of formula 10 can be prepared by $BH_3$ mediated reduction of amides and acids respectively of formula 11 in a solvent such as THF. Compounds of formula 11 can be prepared by nitration of commercially available aryl acetic and hydrocinnamic acids of formula 12 followed by conversion to the corresponding amide if appropriate.

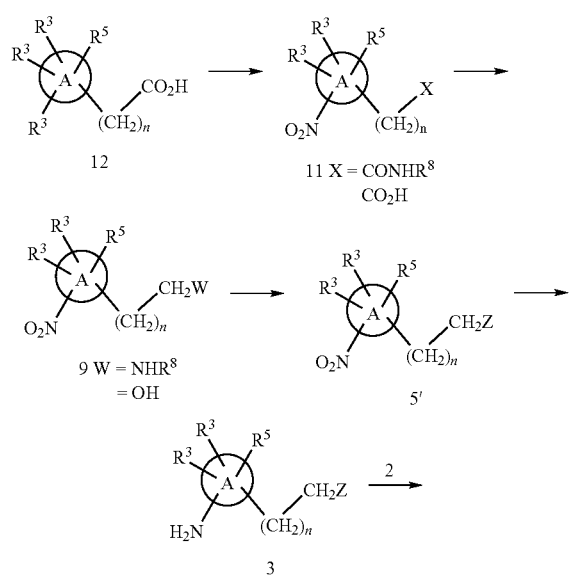

To prepare compounds of formula I for which $D^1$ is a methylene and G is O or S (Scheme 4) may be prepared by alkylation of compounds of formula 13 in a solvent such as DMF in the presence of a base such as NaH or $Cs_2CO_3$ with an agent that will incorporate the fragment $Z-D^2$ required to transform the substituent GH of 13 into $R^4$. Compounds of formula 13 can be prepared by demethylation of compounds of formula 14 with a reagent such as $BBr_3$ in a solvent such as $CH_2Cl_2$. Compounds of formula 14 can be prepared by condensation of compounds of formula 15 with compounds of formula 2. Compounds of formula 15 which are not commercially available can be obtained reduction of aryl nitriles or primary carboxamides of formula 16 with a reducing agent such $LiAlH_4$ or $BH_3$ in a solvent such as THF. Compounds of formula 16 can be prepared from commercially available benzoic acids by procedures known to those skilled in the arts. Compounds of formula 15 may also be prepared by chloromethylation of compounds of formula 17 (R=H) or bromination of compounds of formula 17 (R=Me followed by sequential treatment of the resulting benzylic halide 18 with $NaN_3$ in a solvent such as DMF followed by reduction with either $Ph_3P$ in a solvent such as EtOH or catalytic hydrogenation over Pd in EtOH.

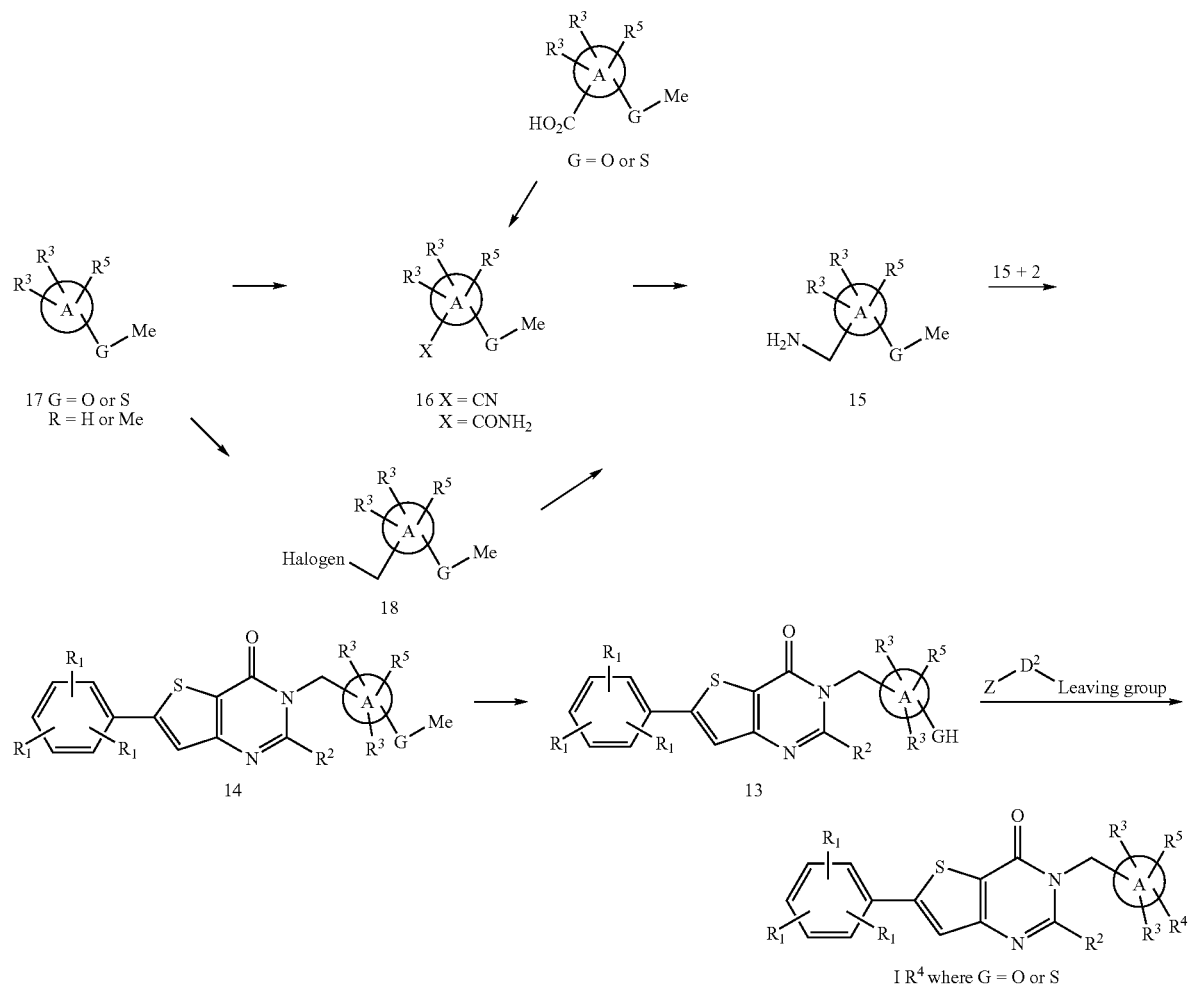

An alternative route (Scheme 5) for preparation compounds of formula I 5 where $D^1$ is a methylene entails alkylation of compounds of formula 19 in a solvent such as DMF containing a base such as $Cs_2CO_3$ with a benzyl halide of formula 20 bearing a fully assembled substituent $R^4$ described by $G-D^2-Z$ or with benzyl halides of formula 18. Conversion of the alkylation product with 18 compounds of formula I may be achieved using procedures described in Scheme for the transformation of 14 to I. Compounds of formula 19 may be prepared as described in WO 03/033476 or by coupling compounds of formula 21 with commercial aryl borates of formula 22 in the presence of catalyst such as $(Ph_3P)_4Pd$ in a solvent such dioxane/ aq $Na_2CO_3$. Compounds of formula 21 may be prepared as described in WO 98/49899.

SCHEME 5

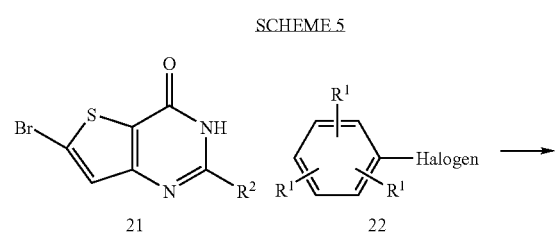

-continued

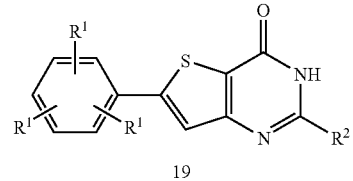

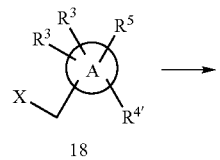

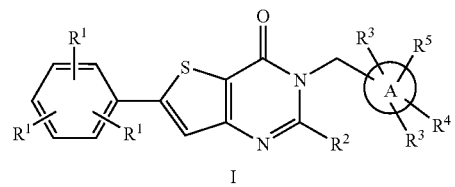

In Scheme 6 compounds of formula I where D is a bond may be prepared by transformation, if necessary, of the substituent $R^{4'}$ of 23 into $R^4$ by sequential deprotection, alkylation and/or acylation using procedures familiar to those skilled in the arts. Compounds of formula 23 can be prepared by arylation of compounds of formula 19 with a aryl borate of formula 22 in the preence of $Cu(OAc)_2$ in a solvent such as $CH_2Cl_2$ containing molecular sieves. Aryl borates of formula 24 are commercially available or can be formed by treating commercially compounds of formula 25 either with n-BuLi in a solvent such as THF followed by sequential addition $BCl_3$ followed by MeOH or alternatively stirring 25 with borate 26 in the presence of a Pd catalyst.

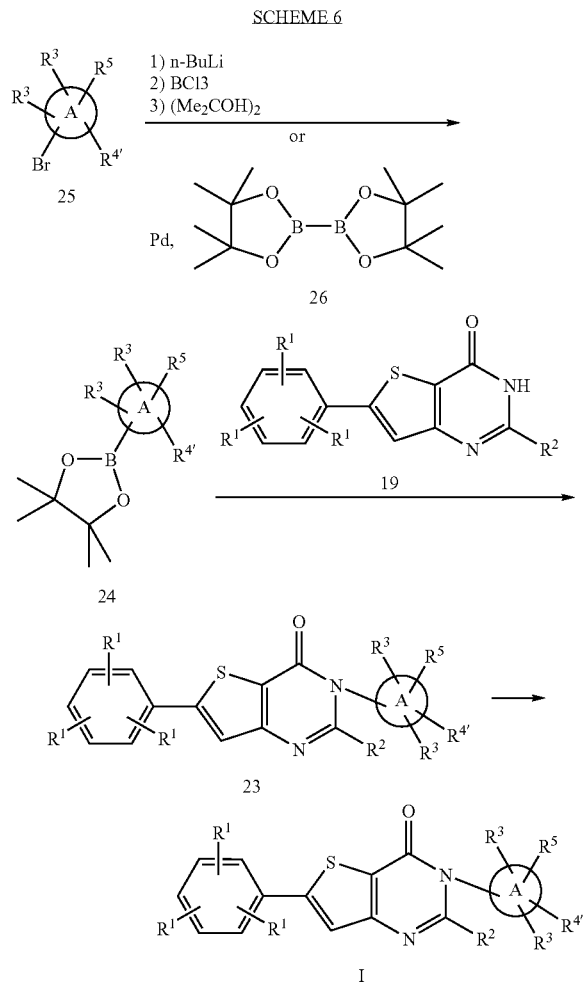

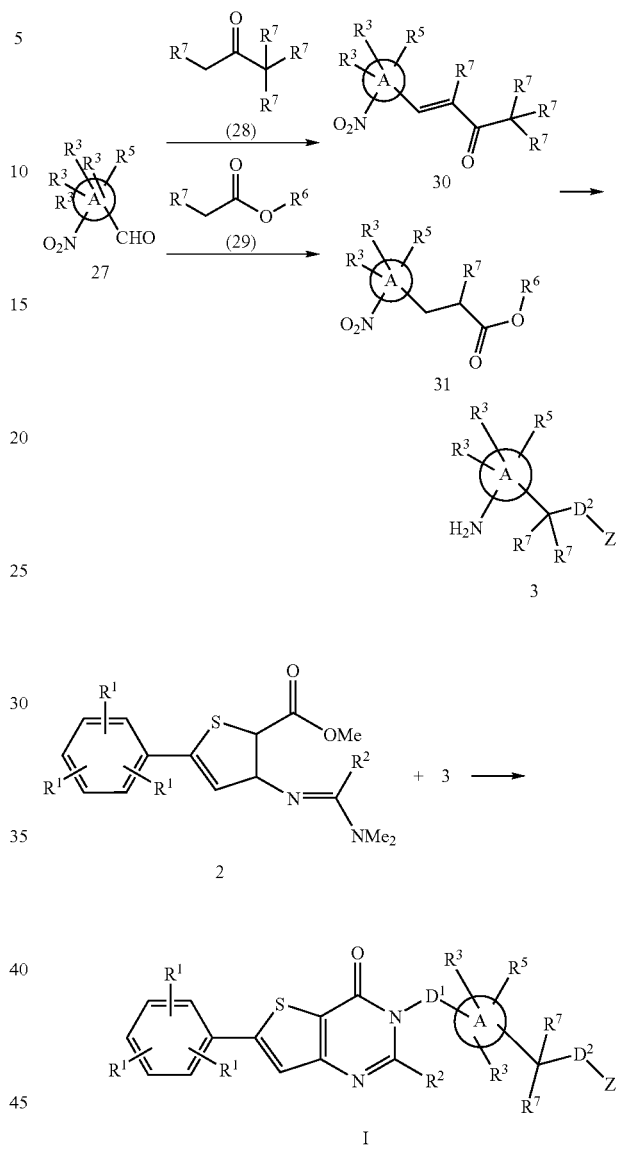

In Scheme 7 compounds of formula I where $G=CH_2$ and D is a bond can be prepared by condensation of the corresponding benzaldehyde of formula 27 with an appropriate ketone of formula 28 or ester of formula 29 in the presence of a base such as NaOH in a solvent such as DMF or EtOH by employing procedures readily known to those skilled in the art. Preparation of compounds of formula 3 where $G=CH_2$ and D is a bond can be completed by reduction of the ketone carbonyl of compounds of formula 30 with a reducing agent such as $NaBH_4$ in a solvent such as EtOH followed by catalyltic hydrogenation using $H_2$ and Pd/C in EtOH or mixtures of EtOH/EtOAc. Alternatively compounds of formula 31 can be transformed to compounds of formula 3 by catalyltic hydrogenation using $H_2$ and Pd/C in EtOH or mixtures of EtOH/EtOAc.

The term "prodrug" encompasses both the term "prodrug esters" and the term "prodrug ethers". The term "prodrug esters" as employed herein includes esters and carbonates formed by reacting one or more hydroxyls of compounds of formula I with either alkyl, alkoxy, or aryl substituted acylating agents or phosphorylating agent employing procedures known to those skilled in the art to generate acetates, pivalates, methylcarbonates, benzoates, amino acid esters, phosphates and the like.

Examples of such prodrug esters include

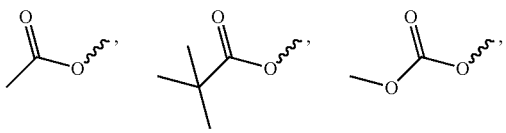

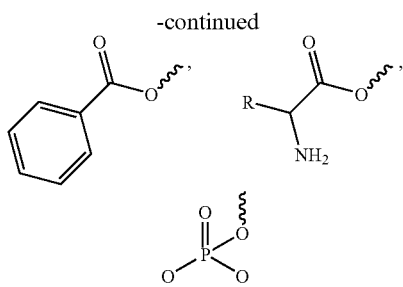

The term "prodrug ethers" include both phosphate acetals and O-glucosides. Representative examples of such prodrug ethers include

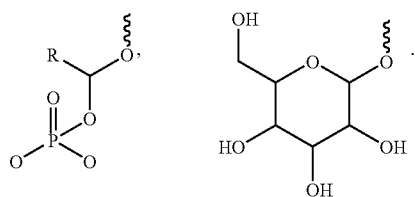

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

All stereoisomers of the compound of the instant application are contemplated, either in admixture or in pure or substantially pure form. The compound of the present application can have asymmetric centers at any of the carbon atoms including any one of the R substituents. Consequently, compound of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

EXAMPLES

The following Examples serve to better illustrate, but not limit, some of the preferred embodiments of the application.

Where possible a modular convergent approach was utilized to prepare the following examples entailing synthesis of the appropriate aniline, condensation with a formamidine to generate the bicyclic thienopyrimidone core followed by subsequent elaboration if required of a side chain. Two conditions were employed to construct the thienopyrimidone bicycle: The aniline and formamidine were heated at reflux in EtOH for 18 hr. Upon cooling the product precipitated and was isolated by filtration. Yields typically were 20-40% and rarely exceeded 40%. Alternatively aniline and formamidine in phenol were heated to 130° C. for 10-30 minutes; following dilution with MeOH, the product was isolated by filtration in yields approaching 80%. Note however, if the product did not precipitate, isolation became tedious and the yields plummeted.

The vast majority of the para alkoxy anilines were either commercially available or synthesized by one of three routes: A, B or C.

Route A (nucleophilic aromatic substitution) required pre-forming the sodium alkoxide with NaH in DMF followed by addition of 2-chloro-5-nitroanisole. Typically the reaction was heated for 1 hr at 90° C. After purification by silica gel chromatography, the nitrated aryl ether was reduced to the desired aniline by 10% Pd/C catalyzed hydrogenation (50 psi $H_2$) in EtOH.

Route B (base promoted phenol alkylation) entailed heating a mixture of the potassium or sodium salt of the nitrophenol with a alkyl halide in DMF for 2-4 hr at 90° C. After isolation and purification by silica gel chromatography, the product was reduced to the desired aniline as previously described.

Route C (base promoted phenol alkylation) was employed when routes A or B were not feasible. A concentrated suspension of the potassium or sodium salt of the phenol, $NaH_2PO_4$ and the appropriate epoxide in 9:1 $MeCN/H_2O$ was heated to 120-180° C. for 30-90 minutes with a microwave or 1-8 hr in steel bomb. (Buffering with $NaH_2PO_4$ is essential to prevent reversion of the product to starting phenol as the pH increases during the reaction. Note even for small scale reactions, temperatures greater than 180° C. should be avoided to minimize the probability of explosive decomposition. For example, the potassium salt of 2-chloro-4-nitrophenol rapidly decomposes at ~210° C. producing gaseous products.) Following isolation and purification by silica gel chromatography, the product was reduced to the desired aniline as previously described.

Several analytical HPLC methods were utilized; all monitored UV absorption at 220 nM:

Method 1. Phenomenex Luna C18 S5 column 4.6×50 mm, 4 min gradient at 4 mL/min, 10% MeOH/90% $H_2O$/0.2% $H_3PO_4$ to 90% MeOH/10% $H_2O$/0.2% $H_3PO_4$ with 1 min hold at the end of the gradient.

Method 2. YMC S5 C18 4.6×50 mm column, 4 min gradient at 4 mL/min, 10% MeOH/90% H₂O/0.2% H₃PO₄ to 90% MeOH/10% H₂O/0.2% H₃PO₄ with 1 min hold at the end of the gradient.

Method 3. Phenomenex S5 C18 4.6×30 mm column, 2 min gradient at 4 mL/min, 10% MeOH/90% H₂O/0.1% TFA to 90% MeOH/10% H₂O/0.1% TFA with 1 min hold at the end of the gradient.

Method 4. Phenomenex S5 C18 4.6×30 mm column, 2 min gradient at 4 mL/min, 10% MeCN/90% H₂O/0.1% TFA to 90% MeCN/10% H₂O/0.1% TFA with 1 min hold at the end of the gradient.

Method 5. Phenomenex Luna C18 S5 column 4.6×50 mm, 4 min gradient at 4 mL/min, 10% MeCN/90% H₂O/0.1% TFA and 90% MeCN/10% H₂O/0.1% TFA with 1 min hold at the end of the gradient.

Method 6. Zorbax SB C18 S5 column 4.6×75 mm, 8 min gradient from 50% solvent B to 100% solvent B at 2.5 mL/min; Solvent A=10% MeOH/90% H₂O/0.2% H₃PO₄; Solvent B=90% MeOH/10% H₂O/0.2% H₃PO₄ with 2 min hold at 100% solvent B.

Method 7. YMC A300-ODS S-5, 4.6 mm×50 mm; 4 min gradient at 4 mL/min.; A=90:10 water:methanol+0.2% phosphoric acid, B=10:90 water:methanol+0.2% phosphoric acid; 0% B to 100% B over 4 min with 1 min hold at the end of the gradient.

Preparative HPLC conditions employed YMC C18 columns using employing gradient elutions with appropriate mixtures of 10% MeOH/90% H₂O/0.1% TFA to 90% MeOH/10% H₂O/0.1% TFA. On occasion, mixtures of 10% MeCN/90% H₂O/0.1% TFA and 90% MeCN/10% H₂O/0.1% TFA were employed. If the molecule contained an acid sensitive component, the TFA was omitted.

Mass spectral data were obtained using a LCMS equipped with a Waters ZMD single quadrapole mass spectrometer. Typical chromatographic conditions for LCMS analyses were Phenomenex reverse phase C18 column 4.6×50 mm, 4 min gradient, 10% MeOH/90% H₂O/0.1% TFA to 90% MeOH/10% H₂O/0.1% TFA, 1 min hold; 4 mL/min, UV detection at 220 nm.

Example 1

Part A.

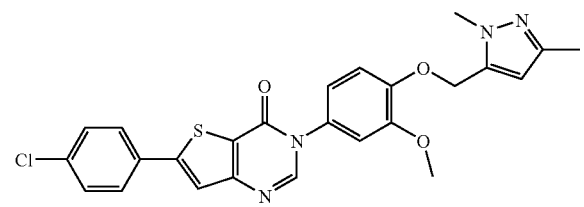

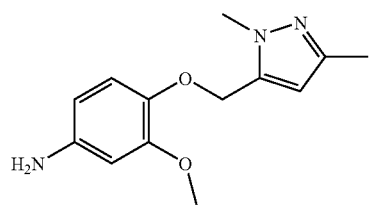

A mixture of nitroguaiacol potassium salt hydrate (1.00 g, 4.83 mmol), 5-(chloromethyl)-1,3-dimethyl-1H-pyrazole (1.0 g. 6.91 mmol) and K₂CO₃ (14.47 g, 1.99 mmol) in dimethylacetamide (35 mL) was stirred at 140° C. for 18 hours. The mixture was diluted with a solution of sat. NaHCO₃, extracted with EtOAc, dried over Na₂SO₄ and concentrated. The crude product was subjected to ISCO flash chromatography (silica gel/hexane-EtOAc 100:0 to 0:100 gradient) to give the title compound (860 mg) as an off-white solid. Following dissolution in MeOH (150 mL) and addition of 10% Pd/C (150 mg), this nitro aryl ether was reduced by stirring under 50 psi H₂ for 3 hours. Filtration and concentration of the filtrate yielded the title compound (660 mg, 58% yield) as an off-white solid. ¹H NMR (400 MHz, CHLOROFORM-D) δ ppm 2.18-2.26 (m, 3H), 3.76-3.84 (m, 3H), 3.85-3.91 (m, 3H), 4.87-4.94 (m, 2H), 5.98-6.04 (m, 1H), 6.17 (d, 1H), 6.29 (d, 1H), 6.73 (d, 1H). HPLC (Method #1): 1.69 min. LCMS m/z: 248 (M+H).

Part B. Methyl 5-(4-chlorophenyl)-3-((dimethylamino)methyleneamino)thiophene-2-carboxylate

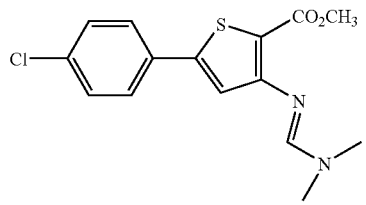

The title compound was prepared following the procedure described in WO2003/033476. Condensation of 2.00 g of methyl 3-amino-5-(4-chlorophenyl)thiophene-2-carboxylate with dimethylformamide dimethyl acetal for 3 hr in refluxing EtOH yielded 2.52 g (100%) after removal of the volatiles under vacuum. ¹H NMR (CDCl₃) δ 3.06 (s, 3H), 3.08 (s, 3H), 3.81 (s, 3H), 6.98 (s, 1H), 7.35 (d, J=8.79 Hz, 2H), 7.53 (d, J=8.24 Hz, 2H), 7.69 (s, 1H); ¹³C NMR (CDCl₃) δ 34.31, 40.26, 51.44, 112.43, 122.28, 126.95, 129.09, 132.18, 134.45, 145.79, 156.09, 159.16, 163.22. HPLC (Method #1): 2.45 min retention time. MS (ES): m/z 323 [M+H]⁺.

Part C.

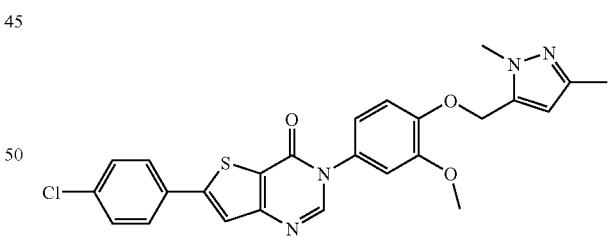

A mixture of the aniline of Part A (46 mg, 0.185 mmol), formamidine of Part B (60 mg, 0.185 mmol) and phenol (700 mg) was stirred at 135° C. for 20 min. The reaction was cooled to room temperature. EtOH (20 mL) was added to the reaction mixture and the precipitated material was filtered, washed with EtOH (20 ml) and dried under vacuum giving the title compound (8 mg) as an off-white solid. ¹H NMR (CDCl₃) δ ppm 2.19-2.32 (m, 3H), 3.87-3.89 (m, 3H), 3.89-3.91 (m, 3H), 5.08-5.13 (m, 2H), 6.10-6.14 (m, 1H), 6.89-7.00 (m, 2H), 7.08 (d, 1H), 7.42-7.48 (m, 2H), 7.52-7.56 (m, 1H), 7.63-7.70 (m, 2H), 8.11-8.16 (m, 1H). HPLC (Method #1): 4.56 min. LCMS m/z: 493 (M+H)

Examples 2 to 5

These examples were prepared analogous to Example 1 using commercially available heteroaryl methyl halides.

| Example # | R | Mass spec M + H | HPLC retention | H NMR |
|---|---|---|---|---|
| 2 | thiazolyl-CH2 | 482 | 2.42 Method #3 | $^1$H NMR (CDCl$_3$) δ ppm 3.79–3.99(m, 3H), 5.08–5.20(m, 2H), 5.25–5.35(m, 1H), 6.08–6.18(m, 1H), 7.12–7.23(m, 1H), 7.23–7.32(m, 13H), 7.45(d, 2H), 7.50–7.59(m, 1H), 7.65(d, 2H), 8.03–8.17(m, 1H) |
| 3 | N-methylimidazolyl-CH2 | 479 | 2.11 Method #3 | $^1$H NMR (CDCl$_3$) δ ppm 3.77–3.83(m, 3H), 3.86–3.93(m, 3H), 5.27–5.34(m, 2H), 6.88–6.93(m, 2H), 6.95–6.99(m, 1H), 6.99–7.03(m, 1H), 7.33(d, 1H), 7.45(d, 2H), 7.51–7.55(m, 1H), 7.66(d, 2H), 8.09–8.16 m, 1H) |
| 4 | dimethylpyrazolyl-CH2 | 493 | 4.57 Method #1 | $^1$H NMR (CDCl$_3$) δ ppm 2.21–2.30(m, 3H), 3.88–3.89(m, 3H), 3.89–3.92(m, 3H), 5.06–5.14(m, 2H), 6.08–6.15(m, 1H), 6.89–7.00(m, 2H), 7.07(d, 1H), 7.43–7.49(m, 2H), 7.52–7.58(m, 1H), 7.63–7.71(m, 2H), 8.08–8.18(m, 1H) |
| 5 | imidazolyl-CH2CH2 | 479 | 2.12 Method #3 | $^1$H NMR (CDCl$_3$) δ ppm 3.87–3.92(m, 2H), 4.31(t, 2H), 4.41(t, 2H), 6.88–6.93(m, 2H), 6.95–6.99(m, 1H), 7.07–7.10(m, 1H), 7.10–7.15(m, 1H), 7.45(d, 2H), 7.51–7.56(m, 1H), 7.62–7.71(m, 3H), 8.07–8.16(m, 1H) |

Examples 6 to 10

These examples were prepared analogous to Part B of Example 1 using commercially available 4-heteroaryl substituted aniline.

| Example # | Ar | Mass spec M + H | HPLC retention | H NMR |
|---|---|---|---|---|
| 6 | 4-(pyridin-4-yl)phenyl | 430 | 213** | $^1$H NMR (CDCl$_3$) δ ppm 4.00–4.13 (m, 2H), 7.12–7.20(m, 2H), 7.33–7.42(m, 4H), 7.45(d, 2H), 7.51–7.57 (m, 1H), 7.66(d, 2H), 8.10–8.17(m, 1H), 8.55(d, 2H) |

| Example # | Ar | Mass spec M + H | HPLC retention | H NMR |
|---|---|---|---|---|
| 7 | | 420 | 2.29** | ¹H NMR (CDCl₃) δ ppm 5.43–5.48(m, 2H), 7.42–7.50(m, 6H), 7.52–7.57 (m, 1H), 7.67(d, 2H), 8.09–8.14(m, 1H), 8.16–8.21(m, 1H) |
| 8 | | 447 | 2.23** | ¹H NMR (CDCl₃) δ ppm 2.15–2.24 (m, 6H), 3.79–3.86(m, 2H), 7.27–7.35(m, 4H), 7.45(d, 2H), 7.51–7.55 (m, 1H), 7.66(d, 2H), 8.10–8.15(m, 1H) |
| 9 | | 416 | 2.11** | ¹H NMR (CDCl₃) δ ppm 7.46(d, 2H), 7.52–7.62(m, 5H), 7.68(d, 2H), 7.82 (d, 2H), 8.16–8.22(m, 1H), 8.73(d, 2H) |
| 10 | | 416 | 2.04** | ¹H NMR (CDCl₃) δ ppm 3.81–3.87 (m, 3H), 7.02–7.05(m, 1H), 7.16–7.19(m, 1H), 7.46(d, 2H), 7.53–7.59 (m, 3H), 7.67(d, 2H), 7.85(d, 2H), 8.15–8.21(m, 1H) |

Example 11

6-(4-Chlorophenyl)-3-(5-(2-hydroxypropoxy)pyridin-2-yl)thieno[3,2-d]pyrimidin4(3H)-one

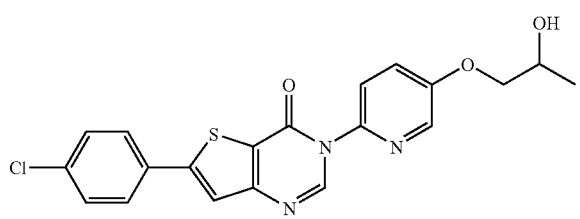

Part A. 6-(4-Chlorophenyl)-3-(5-hydroxypyridin-2-yl)thieno[3,2-d]pyrimidin-4(3H)-one A round bottom flask containing a mixture of the formamidine previously described in Example X (2.0 g, 6.10 mmol), phenol (4.0 g) and 6-aminopyridin-3-ol (0.68 g, 6.10 mmol) was immersed in an oil bath preheated to 130° C. After stirring for 100 min, HPLC analysis revealed virtually all of the two starting components had been consumed. The mixture was allowed to cool to rt; upon dilution with i-PrOH (20 mL) a beige solid formed. After stirring for 5 min, the solid was collected by filtration, washed with i-PrOH and air-dried. Subsequent trituration with i-PrOH (20 mL) removed any trace phenol contaminant yielding the desired product as a white solid (0.85g, 40%) after filtration, washing with i-PrOH and air drying. ¹H NMR (DMSO-D6) δ 7.40 (dd, J=8.6, 3.0 Hz, 1H), 7.58 (d, J=8.3 Hz, 2H), 7.61 (d, J=8.6 Hz, 1H), 7.93 (d, J=8.3 Hz, 1H), 7.98 (s,1H), 8.13 (d, J=3.0 Hz, 1H), 8.53 (s, 1H), 10.46 (s, 1H). MS (ES): m/z 356 [M+H]⁺.

Part B.

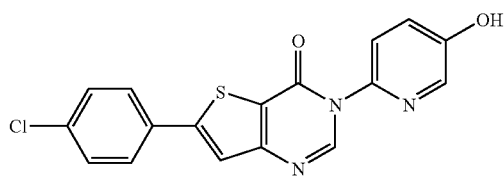

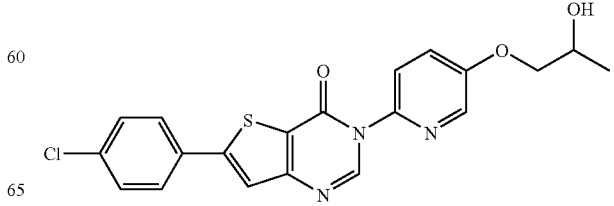

To a mixture of 6-(4-chlorophenyl)-3-(5-hydroxypyridin-2-yl)thieno[3,2-d]pyrimidin-4(3H)-one (200 mg, 0.56 mmol) and $K_2CO_3$ (232 mg, 2.32 momol) in 10:1 $CH_3CN/H_2O$ (5.5 mL) was added propylene oxide (0.39 ml, 5.62 mmol). The mixture was heated to 125° C. in microwave for 30 min, then cooled to rt, diluted with $H_2O$ (10 mL) and extracted with $CH_2Cl_2$ (3×20 mL). The combined $CH_2Cl_2$ solution was washed with brine, dried with $Na_2SO_4$, and concentrated. The resulting brown oil was triturated with MeOH (2 mL) to give 43 mg of title compound as a beige solid. $^1$H NMR (DMSO-D6) δ 1.17 (d, J=6.1 Hz, 3H), 3.98-4.00 (m, 3H), 4.99 (d, J=4.4 Hz, 1H), 7.58 (d, J=8.5 Hz, 2H), 7.66 (dd, J=3.0 Hz, 8.8 Hz, 1H), 7.72 (d, J=8.8 Hz, 1H), 7.92 (d, J=8.5 Hz, 2H), 7.98 (s,1H), 8.32 (d, J=3.0 Hz, 1H), 8.55 (s, 1H). MS (ES): m/z 356 [M+H]$^+$.

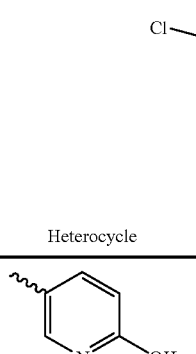

| Example # | Heterocycle | Mass spec M+ | HPLC retention | H NMR | Synthetic Comments |
|---|---|---|---|---|---|
| 12 | 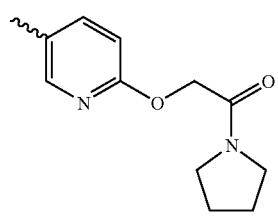 | 340 | 3.30 | $^1$H NMR (CDCl$_3$) δ 7.46(d, J=8.25, 2H), 7.52–7.55(m, 1H), 7.56(s, 1H), 7.67(d, J=8.25Hz, 2H), 7.88(d, J=8.25Hz, 1H), 8.13(s, 1H), 8.72(d, J=2.20Hz, 1H), 8.76(d, J=4.95Hz, 1H) | |
| 13 | 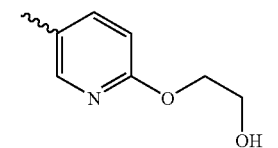 | 467 | 3.55 | $^1$H NMR (CDCl$_3$) δ 1.83–1.89(m, 2H), 1.98–2.03(m, 2H), 3.48–3.53(m, 4H), 4.96 (s, 2H), 7.04(d, J=8.80Hz, 1H), 7.41(d, J=8.25Hz, 2H), 7.49(s, 1H), 7.62(d, J= 8.25Hz, 2H), 7.70(dd, J=8.80Hz, 2.75 Hz, 1H), 8.06(s, 1H), 8.12(d, J=2.75Hz, 1H) | |
| 14 | 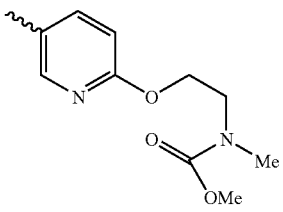 | 400 | 3.43 | $^1$H NMR (DMSO-d$_6$) δ 3.72–3.76(m, 2H), 4.32–4.34(t, 2H), 4.87–4.90(t, 1H), 6.99 (d, J=8.79Hz, 1H), 7.57(d, J=8.35Hz, 2H), 7.93(d, J=8.35Hz, 3H), 7.99(s, 1H) 8.32(d, J=2.64Hz, 1H), 8.45(s, 1H) | |
| 15 | 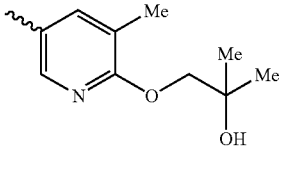 | 471 | 3.74 | $^1$H NMR (DMSO-d$_6$) δ 2.92(s, 3H), 3.52–3.61(m, 5H), 4.44(br s, 2H), 6.99(d, J= 8.80Hz, 1H), 7.57(d, J=7.70Hz, 2H), 7.92–7.99(m, 4H), 8.34(s, 1H), 8.45(s, 1H) | |
| 16 | 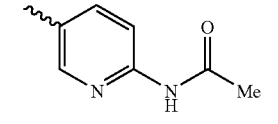 | 442 | 4.30 | $^1$H NMR (400 MHz, CHLOROFORM-D) d ppm 1.81–1.92(m, 2H), 2.31(q, 4H), 3.89(s, 3H), 4.25(s, 2H), 6.88–6.96(m, 2H), 7.04(d, J=8.65Hz, 1H), 7.15–7.21 (m, 1H), 7.45(d, J=8.65Hz, 2H), 7.54(s, 1H), 7.66(d, J=8.65Hz, 2H), 8.16(s, 1H) | |
| 17 | 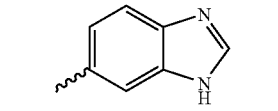 | 397 | 3.87 Method #2 | $^1$H NMR (400 MHz, DMSO-d$_6$) δ 10.77 (1H, s), 8.45–8.52(1H, m), 8.22(1H, d, J=9.16Hz), 7.96–8.02(2H, m), 7.93(2H, d, J=8.65Hz), 7.58(2H, d, J=8.65Hz), 2.13(3H, s) | |
| 18 |  | 379 | 1.63 Method #4 | $^1$H NMR (400 MHz, DMSO-d$_6$) δ 7.59(d, J=8.65Hz, 2H), 7.67(dd, J=8.65, 2.03Hz, 1H), 7.92–7.98(m, 3H), 8.02(s, 1H), 8.09(d, J=2.03Hz, 1H), 8.50(s, 1H), 9.38(s, 1H) | |

-continued

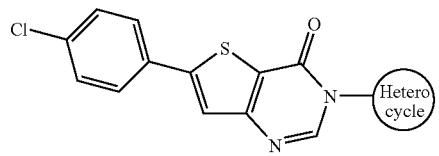

| Example # | Heterocycle | Mass spec M+ | HPLC retention | H NMR | Synthetic Comments |
|---|---|---|---|---|---|
| 19 | (1-Me-benzimidazol-5-yl) | 393 | 1.56 Method #4 | $^1$H NMR (400 MHz, DMSO-$d_6$) δ 3.90(s, 3H), 7.41(dd, J=8.39, 1.78Hz, 1H), 7.59 (d, J=8.14Hz, 2H), 7.73(d, J=8.65Hz, 1H), 7.85(d, J=1.53Hz, 1H), 7.94(d, J=8.65Hz, 2H), 8.00(s, 1H), 8.33(s, 1H), 8.46(s, 1H) | |
| 20 | (1-Et-2-Me-benzimidazol-5-yl) | 421 | 2.48 Method #5 | $^1$H NMR (400 MHz, DMSO-$d_6$) δ 1.32(t, J=7.12Hz, 3H), 2.58(s, 3H), 4.28(q, J=7.12Hz, 2H), 7.31(dd, J=8.65, 2.03Hz, 1H), 7.58(d, J=8.65Hz, 2H), 7.66(d, J=8.65Hz, 1H), 7.70(d, J=1.53Hz, 1H), 7.93(d, J=8.65Hz, 2H), 7.99(s, 1H), 8.45(s, 1H) | |
| 21 | (1-(2-hydroxyethyl)-2-Me-benzimidazol-5-yl) | 437 | 1.54 Method #4 | $^1$H NMR (400 MHz, DMSO-$d_6$) δ 2.89(s, 3H), 3.78–3.86(m, 2H), 4.52–4.61(m, 2H), 7.59(d, J=8.65Hz, 2H), 7.74(dd, J=8.65, 2.03Hz, 1H), 7.94(d, J=8.65Hz, 2H), 8.04(s, 1H), 8.09–8.16(m, 2H), 8.50(s, 1H) | |
| 22 | (1-Me-2-(hydroxymethyl)-benzimidazol-5-yl) | 423 | 2.01 Method #3 | $^1$H NMR (400 MHz, DMSO-$d_6$) δ 3.91(s, 3H), 4.77(d, J=5.60Hz, 2H), 5.67(t, J=5.85Hz, 1H), 7.40(dd, J=8.39, 1.78Hz, 1H), 7.60(d, J=8.14Hz, 2H), 7.71(d, J=8.65Hz, 1H), 7.80(d, J=2.03Hz, 1H), 7.95(d, J=8.65Hz, 2H), 8.01(s, 1H), 8.47(s, 1H) | |
| 23 | (1-Me-2-(1-hydroxyethyl)-benzimidazol-5-yl) | 437 | 2.03 Method #2 | $^1$H NMR (400 MHz, DMSO-$d_6$) δ 1.61(d, J=6.60Hz, 3H), 4.06(s, 3H), 5.41(q, J=6.69Hz, 1H), 7.59(d, J=8.52Hz, 2H), 7.76(dd, J=8.66, 1.51Hz, 1H), 7.94(d, J=8.52Hz, 2H), 8.02(s, 1H), 8.03(d, J=1.65Hz, 1H), 8.10(d, J=8.80Hz, 1H), 8.49(s, 1H) | |
| 24 | (1-(2-hydroxy-2-methylpropyl)-benzimidazol-5-yl) | 451 | 2.11 Method #2 | $^1$H NMR (400 MHz, DMSO-$d_6$) δ 1.10(s, 6H), 4.17(s, 2H), 4.80(s, 1H), 7.32(dd, J=8.65, 2.03Hz, 1H), 7.59(d, J=8.65Hz, 2H), 7.77(d, J=8.65Hz, 1H), 7.89–7.98 (m, 3H), 8.01(s, 1H), 8.26(s, 1H), 8.48 (s,1H) | Method C used to prepare ArNH$_2$ |
| 25 | (1-(2-hydroxy-2-methylpropyl)-benzimidazol-6-yl) | 451 | 2.09 Method #2 | 1H NMR (400 MHz, Solvent) d ppm 1.13 (s, 6H), 4.22(s, 2H), 4.84(s, 1H), 7.37 (dd, J=8.65, 2.03Hz, 1H), 7.59(d, J=8.65 Hz, 2H), 7.78–7.86(m, 2H), 7.94(d, J=8.65Hz, 2H), 8.00(s, 1H), 8.26(s, 1H), 8.48(s, 1H) | Method C used to prepare ArNH2 |

Example 26

6-(4-Chlorophenyl)-3-(5-(2-hydroxypropylthio)-1,3,4-thiadiazol-2-yl)thieno[3,2-d]pyrimidin-4-(3H)-one

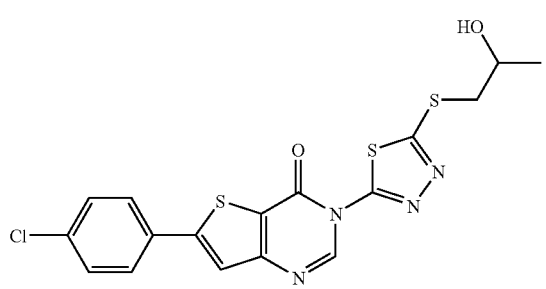

Part A. 1-(5-Amino-1,3,4-thiadiazol-2-ylthio)propan-2-one

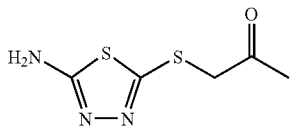

A mixture of 5-amino-1,3,4-thiadiazole-2-thiol (1.0 g, 7.5 mmol), NaOH (0.330 g, 8.3 mmol) and 1-chloropropan-2-one (0.581 mL, 7.3 mmol) in EtOH (2.1 mL) and H$_2$O (2.1 mL) was heated at 80° C. for 2 h. The solution was cooled to rt, diluted with H$_2$O and the tan solid which precipitated filtered, washed with water and air dried under vacuum to afford the title compound (0.720 g). $^1$H NMR (CDCl$_3$) δ 2.35 (s, 3H), 4.08 (s, 2H), 5.00 (s, 2H). HPLC (Method #1) 0.610 min retention time, (90%). MS (ES): m/z 190 [M+H]$^+$.

Part B. 1-(5-Amino-1,3,4-thiadiazole-2-ylthio)propan-2-ol

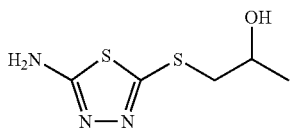

To a mixture of 1-(5-amino-1,3,4-thiadiazol-2-ylthio)propan-2-one (700 mg, 3.7 mmol) in 8 mL of 1:1 MeOH/H$_2$O at rt was added a solution of NaBH$_4$ (159 mg, 4.2 mmol) in 1.5 mL of H$_2$O dropwise over 10 min. The suspension was stirred at rt for 1 h and diluted with 0.6 mL of HOAc followed by 6 mL of H$_2$O. The precipitate was filtered, washed with H$_2$O and dried under vacuum to afford 0.608 g of the title compound (86%) as an off-white solid. $^1$H NMR (400 MHz, MeOH-d$_3$) δ 1.25 (d, J=6.6 Hz, 3H), 3.06-3.21 (m, 2H), 3.90-4.04 (m, 1H). HPLC (Method #1) 0.710 min retention time, (90%). MS (ES): m/z 192 [M+H]$^+$.

Part C.

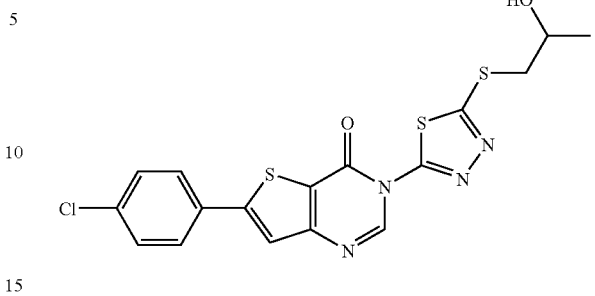

A mixture of the formamidine of Example 1 (0.845 g, 2.62 mmol), 1-(5-amino-1,3,4-thiadiazol-2-ylthio)propan-2-ol (0.500 g, 2.62 mmol) and 3.0 g of phenol was heated at 130° C. for 0.75 h. The solution was cooled to rt, diluted with ethanol and the yellow solid which precipitated filtered, washed with ethanol and air dried under vacuum. The solid was triturated in acetic acid and a light yellow solid filtered, washed with ethanol and air dried under vacuum to afford the title compound (0.452 g). $^1$H NMR (500 MHz, DMSO-d$_6$) δ 1.20 (d, J=6.0 Hz, 3H), 3.29-3.36 (m, 1H), 3.37-3.45 (m, 4H), 3.93-4.02 (m, 1H), 5.18 (d, J=4.9 Hz, 1H), 7.59 (d, J=8.8 Hz, 2H), 7.95 (d, J=8.8 Hz, 2H), 8.08 (s, 1H), 9.29 (s, 1H). HPLC (Method #1) 4.07 min retention time, (93%). MS (ES): m/z 437 [M+H]$^+$.

Pro-drugs were prepared of selected alcohols to improve solubility and exposure. Standard conditions, employed to generate amino acid esters of all but the glycine ester of the tertiary alcohols, are described in application ## as are the half ester of dibasic acids.

| Pro-drug | Mass spec M+ | HPLC retention | H NMR |
|---|---|---|---|
| Glutarate half ester of Example 22 | 537 | 3.72 Method #2 | $^1$H NMR(400MHz, DMSO-d$_6$) δ 1.61–1.73(m, 2H), 1.87(t, J=7.12Hz, 2H), 2.38(t, J=7.63Hz, 2H), 3.88(s, 3H), 5.37(s, 2H), 7.43(dd, J=8.65, 2.03Hz, 1H), 7.58(d, J=8.65Hz, 2H), 7.74(d, J=8.65Hz, 1H), 7.83(d, J=1.53Hz, 1H), 7.93(d, J=8.14Hz, 2H), 7.99(s, 1H), 8.46(s, 1H) |
| Succinate half ester of Example 22 | 523 | 3.67 Method #2 | $^1$H NMR(400MHz, DMSO-d$_6$) δ 2.09(t, J=7.12Hz, 2H), 2.41(t, J=6.87Hz, 2H), 3.88(s, 3H), 5.32(s, 2H), 7.43(d, J=8.14Hz, 1H), 7.58(d, J=8.14Hz, 2H), 7.74(d, J=8.65Hz, 1H), 7.83(s, 1H), 7.94(d, J=8.65Hz, 2H), 8.00(s, 1H), 8.46(s, 1H) |
| Valine Ester of Example 22 | 522 | 3.49 Method #2 | $^1$H NMR(400MHz, MeOD) δ 1.11(d, J=7.12Hz, 3H), 1.13(d, J=8.65Hz, 3H), 2.39–2.49(m, 1H), 4.22(singlet overlapping a multiplet, 4H), 5.85(d, J=15.01Hz, 1H), 6.01(d, J=15.01Hz, 1H), 7.53(d, J=8.65Hz, 2H), 7.77(s, 1H), 7.81–7.88(m, 3H), 8.13–8.19(m, 2H), 8.53(s, 1H) |

Biological Evaluation

Radioligand Binding Assay for Assessment of MCHR1 Activity

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl2, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC Unifilter plates pre-coated with 0.075 ml binding buffer containing 1% BSA, and washed 3 times with 0.4 ml of Phospho-buffered Saline (pH 7.4) containing 0.01% TX-100. Filters were dried, 0.05 ml microscint 20 was added to each well and radioactivity was subsequently quantified by scintillation counting on a TopCount™ microplate scintillation counter (Packard). Inhibitory constants were determined by nonlinear least squares analysis using a four parameter logistic equation.

Utilities and Combinations

Utilities

The compounds of the present application can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease.

The compounds described in the present application could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present application include donepezil, tacrine, revastigraine, 5HT6, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

Combinations

The present application includes within its scope pharmaceutical compositions comprising, as an active ingredient, a therapeutically effective amount of at least one of the compounds of formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the melanin-concentrating hormone receptor (MCHR) antagonists in accordance with the application.

Examples of suitable anti-obesity agents for use in combination with the compounds of the present application include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present application include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594, 016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present application may be employed with a PPARα/γ dual agonist such as MK-767/KRP-297 (Merck/Kyorin; as described in, K. Yajima, et. al., *Am. J. Physiol. Endocrinol. Metab.*, 284: E966-E971 (2003)), AZ-242 (tesaglitazar; Astra-Zeneca; as described in B. Ljung, et. al., *J. Lipid Res.*, 43, 1855-1863 (2002)); muraglitazar; or the compounds described in U.S. Pat. No. 6,414,002.

The compounds of the present application may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.*, 31, 1869-1871 (1998) including isoprenoid (phosphinyl-methyl)phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al., *J. Med. Chem.*, 20, 243-249 (1977), the famesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24, 9-15 (1999), (Avasimibe); "The ACAT inhibitor, Cl-1011 is effective in the prevention and regression of aortic fatty streak area in hamsters", Nicolosi et al., *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al., *Bioorg. Med. Chem. Let.*, 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors: potential anti-atherosclerotic agents", Sliskovic et al., *Curr. Med. Chem.*, 1 (3), 204-25 (1994); "Inhibitors of acyl-CoA:cholesterol β-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.*, 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present application may be employed in combination with anti-hypertensive agents. Examples of suitable anti-hypertensive agents for use in combination with the compounds of the present application include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

It should be understood that while this application has been described herein in terms of specific embodiments set forth in detail, such embodiments are presented by way of illustration of the general principles of the application, and the application is not necessarily limited thereto. Certain modifications and variations in any given material, process step or chemical formula will be readily apparent to those skilled in the art without departing from the true spirit and scope of the present application, and all such modifications and variations should be considered within the scope of the claims that follow.

What is claimed is:

1. A compound selected from the group consisting of:

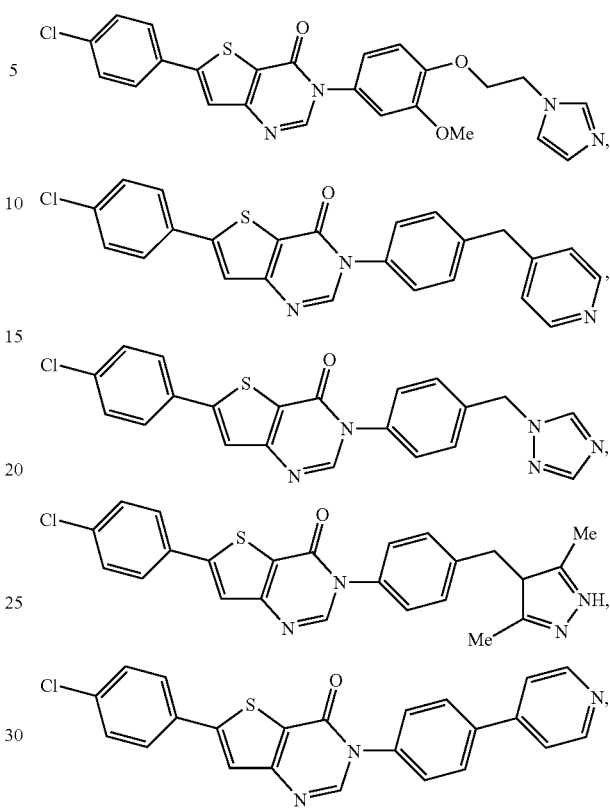

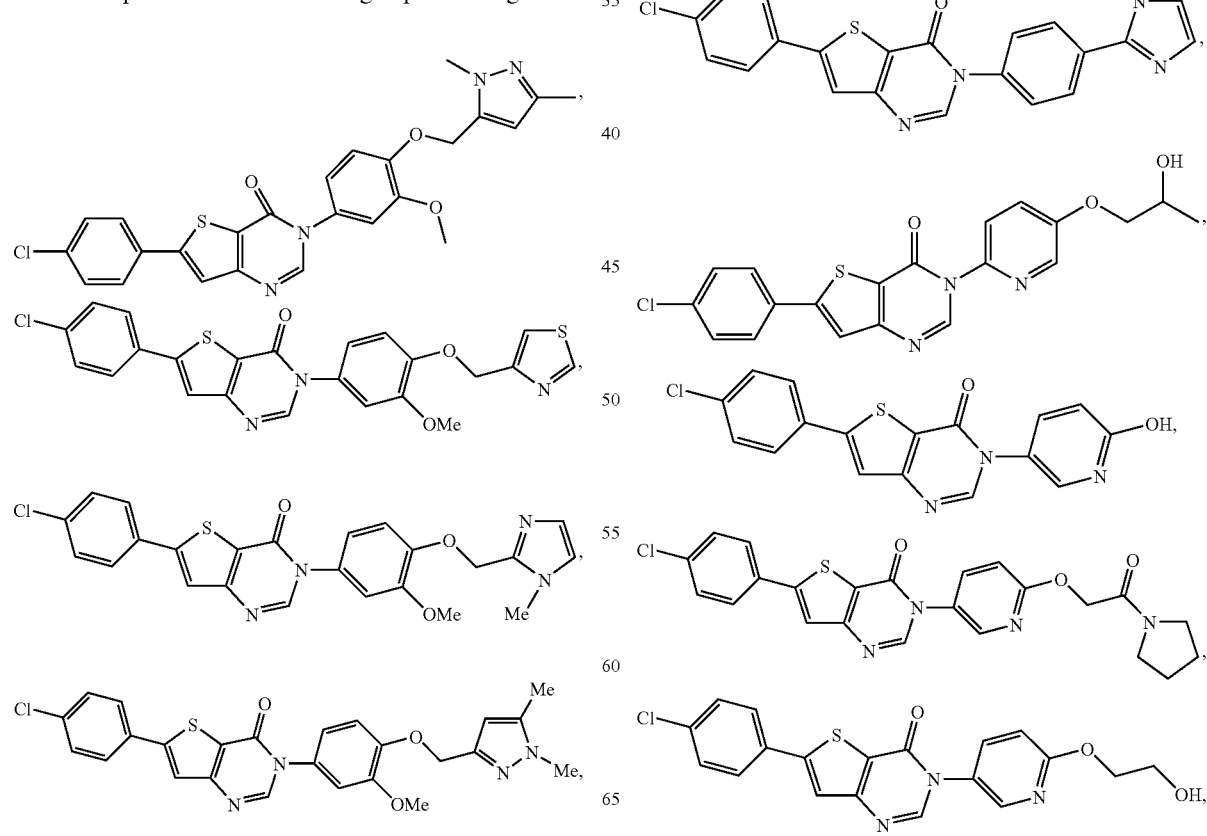

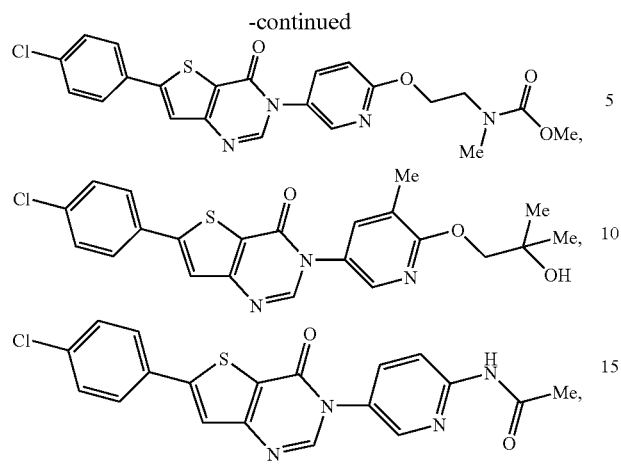
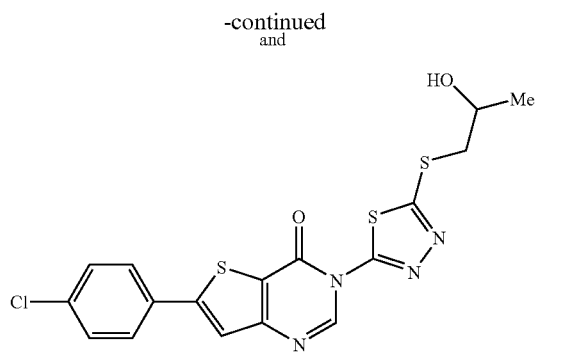
or an amino acid ester prodrug of any of the preceding compounds.
\* \* \* \* \*

UNITED STATES PATENT AND TRADEMARK OFFICE
CERTIFICATE OF CORRECTION

PATENT NO. : 7,745,447 B2  Page 1 of 1
APPLICATION NO. : 11/586147
DATED : June 29, 2010
INVENTOR(S) : William N. Washburn, Saleem Ahmad and Khehyong Ngu It is certified that error appears in the above-identified patent and that said Letters Patent is hereby corrected as shown below:

Title Page, Col. 1 (Other Publications)

Line 3, "Bioroganic" should read -- Bioorganic --; and

Line 3, "Chemsitry" should read -- Chemistry --.

Column 36

Line 20-25, " 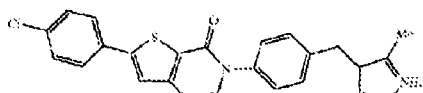 " should read

-- 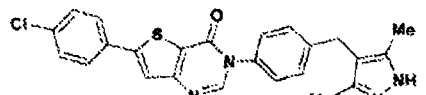 --.

Signed and Sealed this

Twenty-sixth Day of October, 2010

David J. Kappos
*Director of the United States Patent and Trademark Office*